US00PP31871P2

(12) United States Plant Patent
Osiecki

(10) Patent No.: US PP31,871 P2
(45) Date of Patent: Jun. 16, 2020

(54) ***MANDEVILLA* PLANT NAMED 'MOGI THREE'**

(50) Latin Name: *Mandevilla hybrida*
Varietal Denomination: MOGI THREE

(71) Applicant: Oglesby Plants International, Inc., Altha, FL (US)

(72) Inventor: Marian Osiecki, Marianna, FL (US)

(73) Assignee: Oglesby Plants International, Inc., Altha, FL (US)

( * ) Notice: Subject to any disclaimer, the term of this patent is extended or adjusted under 35 U.S.C. 154(b) by 0 days.

(21) Appl. No.: 16/602,010

(22) Filed: Jul. 18, 2019

(51) Int. Cl.
*A01H 5/02* (2018.01)
*A01H 6/08* (2018.01)

(52) U.S. Cl.
USPC ..... Plt./232
CPC ..... *A01H 6/088* (2018.05)

(58) Field of Classification Search
USPC ..... Plt./232
CPC ..... A01H 5/02
See application file for complete search history.

*Primary Examiner* — Kent L Bell
(74) *Attorney, Agent, or Firm* — Cassandra Bright

(57) ABSTRACT

A new and distinct *Mandevilla* cultivar named 'MOGI THREE' is disclosed, characterized by short internodes, light pink flowers, and glossy foliage. Plants grow vigorously and flower abundantly. The new variety is a *Mandevilla*, typically produced as an indoor ornamental plant.

2 Drawing Sheets

Figure 1:
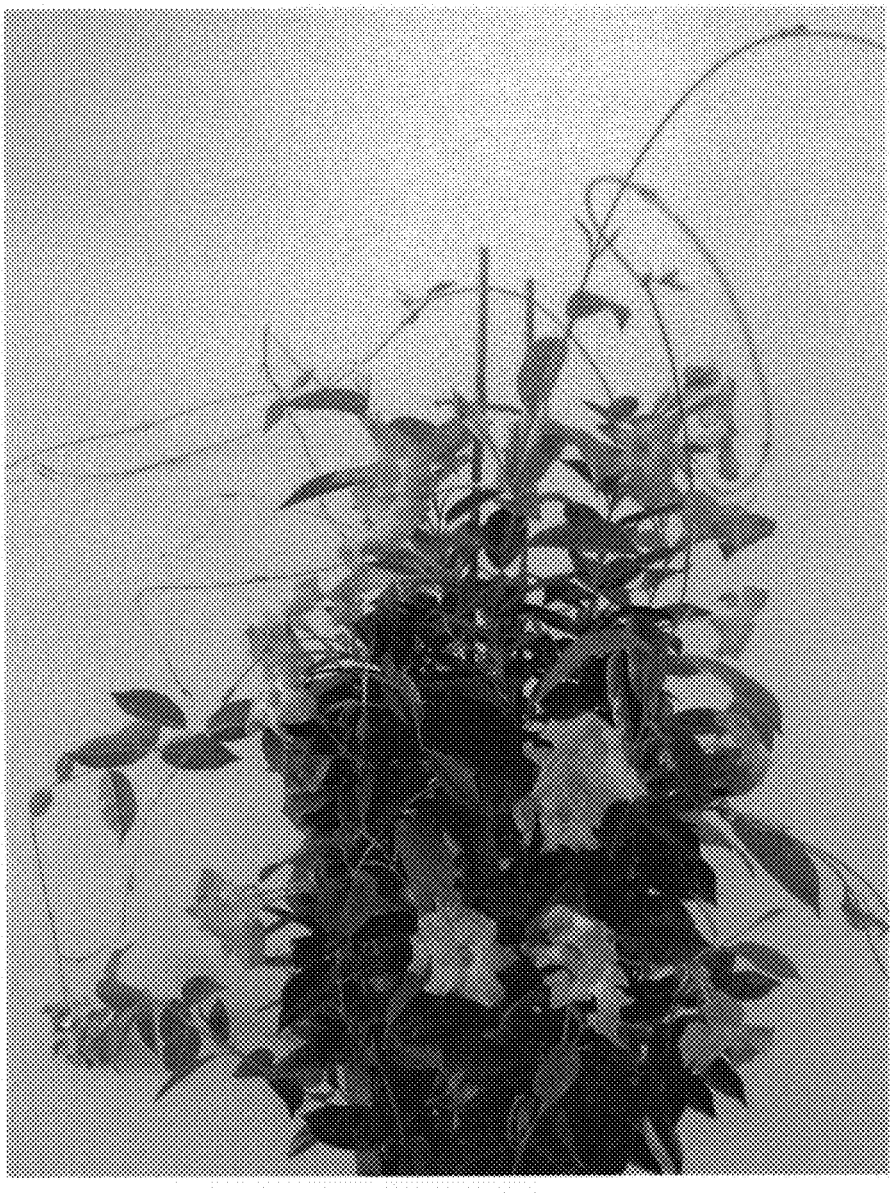

Latin name of the genus and species: *Mandevilla hybrida*.
Variety denomination: 'MOGI THREE'.

BACKGROUND OF THE INVENTION

The new cultivar is a product of a planned breeding program. The objective of the breeding program was to develop new *Mandevilla* varieties with vigorous plant habits suitable for commercial production. The new variety originated from a cross pollination of an unnamed proprietary, unpatented seed parent and the pollen parent, a different, unnamed proprietary, unpatented *Mandevilla*. The crossing was made during March 2013.

The new variety was discovered by the inventor, Marian Osiecki in the Summer of 2014 in a group of seedlings resulting from the crossing. The new cultivar was found in a commercial greenhouse in Altha, Fla.

Asexual reproduction of the new cultivar 'MOGI THREE' was first performed at a commercial laboratory in Altha, Fla. by terminal vegetative cuttings in August 2014. Subsequent propagation by tissue culture has shown that the unique features of this cultivar are stable and reproduced true to type in successive generations.

SUMMARY OF THE INVENTION

The cultivar 'MOGI THREE' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'MOGI THREE'. These characteristics in combination distinguish 'MOGI THREE' as a new and distinct *Mandevilla* cultivar:

1. Light pink flowers.
2. Vigorous plants
3. Rapid growth.

4. Short internodes.
5. Abundant flowering.
6. Dense branching.
7. Suitable for trellis production or hanging baskets.

PARENT COMPARISON

Plants of the new cultivar 'MOGI THREE' are similar to the seed parent in most horticultural characteristics. The new variety, however, differs in the following:

1. Plants of the new variety are denser and bushier than plants of the seed parent.
2. 'MOGI THREE' produces lighter pink flowers than the seed parent.
3. 'MOGI THREE' flowers more abundantly than the seed parent.

Plants of the new cultivar 'MOGI THREE' are similar to the pollen parent in most horticultural characteristics. Plants of the new variety however differ in the following:

1. MOGI THREE' is more vigorous than the pollen parent.
2. 'MOGI THREE' produces light pink flowers, the pollen parent produces red flowers.

COMMERCIAL COMPARISON

'MOGI THREE' can be compared to the commercial variety *Mandevilla* 'Alice Dupont', unpatented. Plants of 'Alice Dupont' are similar to plants of 'MOGI THREE' in most horticultural characteristics, however, plants of 'MOGI THREE' differ in the following:

1. The new variety produces lighter pink flowers than this comparator.
2. Plants of 'MOGI THREE' are denser and bushier than this comparator.
3. 'MOGI THREE' produces more flowers than this comparator.

'MOGI THREE' can also be compared to the commercial variety *Mandevilla* 'Sunparaprero' U.S. Plant Pat. No.

19,399. Plants of 'Sunparaprero' are similar to plants of 'MOGI THREE' in most horticultural characteristics, however, plants of 'MOGI THREE' differ in the following:

1. The new variety produces lighter pink flowers than this comparator.
2. Plants of 'MOGI THREE' are denser and bushier than this comparator.

BRIEF DESCRIPTION OF THE PHOTOGRAPHS

The accompanying photograph in FIG. 1 illustrates in full color a typical plant of 'MOGI THREE' grown in a greenhouse in Altha, Fla. This plant is approximately 14 months old, shown in an 8 inch pot.

Figure 2:
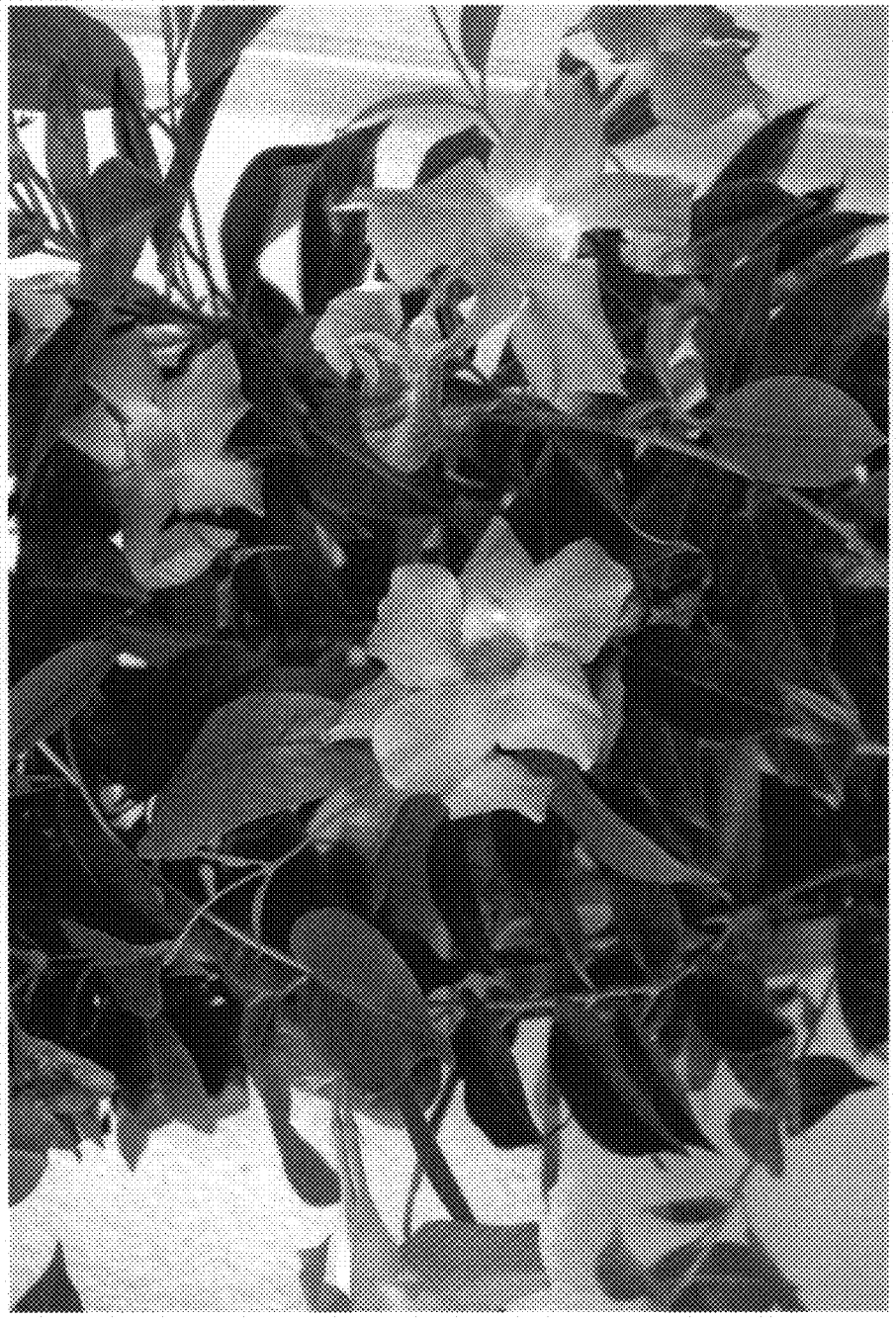

FIG. 2 illustrates a close up view of the flowers.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'MOGI THREE' plants grown in a climate controlled greenhouse in Altha, Fla., USA. Temperatures ranged from 20° C. to 25° C. at night to 25° C. to 32° C. during the day. No artificial light, photoperiodic treatments were given to the plants. Measurements and numerical values represent averages of typical plant types.

Botanical classification: *Mandevilla hybrida* 'MOGI THREE'.

PROPAGATION

Time to initiate roots: About 15 days at approximately 30° C. in the summer. About 25 days at 18° in the winter.

Time to produce a rooted cutting: About 50 days at 20 to 30° C.

Root description: Freely branching and white-brown in color. Not accurately measured with R.H.S. chart.

PLANT

Growth habit: Vining evergreen flowering plant. Initially upright, then vining, requiring support to maintain upright habit. Typically, plants are pinched approximately 3 months after planting a rooted cutting to encourage branching.

Age of plant described: 10 months.

Container size: 3 gallon.

Height: Approximately 83 cm.

Plant spread: Approximately 74 cm.

Growth rate: Moderate.

Branching characteristics: Vigorous branching occurs after pinch.

Length of primary lateral branches: Approximately 31 cm.

Diameter of lateral branches: Approximately 0.8 cm.

Lateral branch color: Near RHS Grey-Brown 199B.

Internode length: Approximately 1.9 cm.

Stem texture: Glabrous.

FOLIAGE

Leaf:

- *Arrangement*.—Opposite, simple.
- *Average length*.—Approximately 9.5 cm.
- *Average width*.—Approximately 4.9 cm.
- *Shape of blade*.—Elliptic.
- *Apex*.—Acute to Cuspidate.
- *Base*.—Obtuse.
- *Attachment*.—Petiolate.
- *Margin*.—Entire.
- *Texture of top surface*.—Glabrous. Glossy.
- *Texture of bottom surface*.—Glabrous. Matte.
- *Leaf internode length*.—Approximately 2.6 cm.
- *Color*.—Young foliage upper side: Near RHS Green 137A. Young foliage under side: Near RHS Green 138B. Mature foliage upper side: Near RHS Green 137A. Mature foliage under side: Near RHS Green 138B.
- *Venation*.—Type: Pinnate. Venation color upper side: Near RHS Yellow-Green 144A. Venation color under side: Near RHS Yellow-Green 139A.
- *Petiole*.—Average Length: Approximately 1.7 cm. Color: Near RHS Yellow-Green 144B. Diameter: Approximately 0.2 cm. Texture: Glabrous.

FLOWER

Natural flowering season: Naturally flower summer through late Autumn.

Inflorescence type and habit: Single salverform flower; terminal or axillary; flowers face mostly outward.

Rate of flower opening: Approximately 6 days from bud to fully opened flower.

Flower longevity on plant: 4 to 5 days, after fully opened. Self-cleaning.

Quantity of flowers: Free flowering, young plants have at least 20 to 35 flowers at all times;

Inflorescence size:

- *Diameter*.—Approximately 7.9 cm.
- *Length*.—Approximately 6.7 cm.
- *Corolla tube length*.—Approximately 5.6 cm.
- *Corolla tube diameter*.—Average 9 mm.
- *Corolla tube texture*.—Glabrous.
- *Throat diameter*.—Approximately 1.6 cm.

Corolla:

- *Petal arrangement*.—Single whorl of 5 imbricate petals, fused into flared trumpet.
- *Size*.—Lobe Length: 2.9 cm. Lobe Width: 2.7 cm.
- *Margin*.—Entire.
- *Apex*.—Rounded, slightly undulate.
- *Texture*.—Smooth, velvety.

Color: Petals:

- *When opening*.—Upper surface: Near RHS Red-Purple 62A with streaks near RHS Red-Purple 62D. Lower surface: Near RHS Red-Purple 62C with steaks of White 155D.
- *Fully opened*.—Upper surface: Near RHS Red-Purple 63C, with streaks near RHS Red-Purple 62D. Lower surface: Near RHS Red-Purple 62C with streaks near RHS Red-Purple 69D. Tube color (exterior): Near RHS Yellow-Green 145D. Tube color (interior): Near RHS Yellow 13A with streaks of Yellow- Orange 22A. Throat color: Near RHS Yellow 9B. Color Changes when Aging: Color becomes lighter, Red-Purple 62D.

Bud:

*Shape*.—Ovate to Lanceolate.

*Length*.—Approximately 7.1 cm.

*Diameter*.—Approximately 1.3 cm.

*Color*.—Near RHS Yellow-Green 145C at base; near RHS Yellow-Green 145D in middle; near RHS Red-Purple 68C with streaks near RHS White 155D at apex.

*Sepals*.—Arrangement: 5 per flower in a single whorl; fused. Shape: Narrowly deltoid. Quantity: 5. Length: Approximately 0.6 cm. Width: Approximately 0.2 cm. Margin: Entire. Apex: Acuminate. Texture: Smooth, waxy. Color: Upper surface: Near RHS Green 138C. Lower surface: Near RHS Green 138D.

Peduncles:

*Length*.—Approximately 1.5 cm.

*Width*.—Approximately 0.23 cm.

*Aspect*.—Almost straight.

*Strength*.—Flexible and strong.

*Color*.—Near RHS Green 138B.

*Texture*.—Glabrous.

Fragrance: Very faint, pleasant fragrance.

REPRODUCTIVE ORGANS

Stamens:

*Number*.—5, anthers fused together at tips, filaments fused to corolla.

*Anther length*.—0.78 cm.

*Anther color*.—Near RHS Yellow 4D.

*Anther shape*.—Oblong.

*Pollen*.—None observed.

Pistil:

*Number*.—1.

*Length*.—Approximately 2.8 cm.

*Style color*.—Near RHS White 155D.

*Stigma*.—Shape: Glabrous. Color: Near RHS White 157D.

*Ovary color*.—Near RHS Green 138B.

OTHER CHARACTERISTICS

Disease resistance: Improved resistance to normal diseases of *Mandevilla* have been observed.

Drought tolerance and cold tolerance: Tolerates temperatures from approximately 0° C. to 40° C. and does not tolerate drought.

Fruit/seed production: Not observed.

What is claimed is:

1. A new and distinct cultivar of *Mandevilla* plant named 'MOGI THREE' as herein illustrated and described.

* * * * *